United States Patent
Farr et al.

(10) Patent No.: US 12,330,150 B2
(45) Date of Patent: Jun. 17, 2025

(54) SYSTEM AND APPARATUS FOR FLUID SAMPLE DELIVERY

(71) Applicant: S.C.R. (Engineers) Limited, Netanya (IL)

(72) Inventors: Vicki Clare Farr, Hamilton (NZ); Paul Trevor Johnstone, Hamilton (NZ); Robert Graham Orchard, Hamilton (NZ)

(73) Assignee: S.C.R (Engineers) Limited, Netanya (IL)

( * ) Notice: Subject to any disclaimer, the term of this patent is extended or adjusted under 35 U.S.C. 154(b) by 899 days.

(21) Appl. No.: 17/262,061

(22) PCT Filed: Jul. 24, 2019

(86) PCT No.: PCT/NZ2019/050086
§ 371 (c)(1),
(2) Date: Jan. 21, 2021

(87) PCT Pub. No.: WO2020/022910
PCT Pub. Date: Jan. 30, 2020

(65) Prior Publication Data
US 2021/0308665 A1    Oct. 7, 2021

(30) Foreign Application Priority Data
Jul. 24, 2018    (NZ) .................................... 744562

(51) Int. Cl.
*B01L 3/02*        (2006.01)
*G01F 11/12*    (2006.01)
(Continued)

(52) U.S. Cl.
CPC ........... *B01L 3/0293* (2013.01); *B01L 3/0262* (2013.01); *G01F 11/125* (2013.01); *G01N 1/14* (2013.01);
(Continued)

(58) Field of Classification Search
CPC ................. B01L 3/0293; B01L 3/0262; B01L 2200/0605; B01L 2200/141;
(Continued)

(56) References Cited

U.S. PATENT DOCUMENTS

| | | |
|---|---|---|
| 4,817,443 A | 4/1989 | Champseix et al. |
| 5,114,350 A | 5/1992 | Hewett |

(Continued)

FOREIGN PATENT DOCUMENTS

| | | |
|---|---|---|
| WO | 2004057305 | 7/2004 |
| WO | 2004102183 | 11/2004 |

(Continued)

*Primary Examiner* — Jill A Warden
*Assistant Examiner* — Alex Ramirez
(74) *Attorney, Agent, or Firm* — Keith O'Doherty

(57) ABSTRACT

Systems and methods for analysing a fluid are disclosed, including a fluid sample delivery apparatus. The system includes a sensing element configured to respond to at least one analyte in a sample of fluid. A detector is provided, configured to sense the response to the analyte by the sensing element. The fluid sample delivery apparatus includes a dosage needle configured to deliver the sample of fluid to the sensing element, at least one pump configured to control flow of fluid through the dosage needle, and at least one actuator configured to move the dosage needle relative to the sensing element. At least one controller is provided, configured to control the at least one pump and the at least one actuator.

15 Claims, 11 Drawing Sheets

(51) Int. Cl.
  *G01N 1/14*    (2006.01)
  *G01N 1/28*    (2006.01)
  *G01N 21/78*   (2006.01)
  *G01N 33/04*   (2006.01)
  *G01N 35/10*   (2006.01)

(52) U.S. Cl.
  CPC ............ *G01N 1/2813* (2013.01); *G01N 21/78* (2013.01); *G01N 33/04* (2013.01); *G01N 35/1011* (2013.01); *G01N 35/1016* (2013.01); B01L 2200/0605 (2013.01); B01L 2200/141 (2013.01); B01L 2300/0663 (2013.01); B01L 2300/069 (2013.01); B01L 2300/14 (2013.01); B01L 2400/024 (2013.01); B01L 2400/0406 (2013.01); B01L 2400/0605 (2013.01); G01N 2001/1427 (2013.01); G01N 2001/2826 (2013.01)

(58) Field of Classification Search
  CPC ....... B01L 2300/0663; B01L 2300/069; B01L 2300/14; B01L 2400/024; B01L 2400/0406; B01L 2400/0605; G01F 11/125; G01N 1/14; G01N 1/2813; G01N 21/78; G01N 33/04; G01N 35/1011; G01N 35/1016; G01N 2001/1427; G01N 2001/2826
  See application file for complete search history.

(56) References Cited

U.S. PATENT DOCUMENTS

| | | |
|---|---|---|
| 5,186,194 A | 2/1993 | Kitajima |
| 5,603,342 A | 2/1997 | Shambaugh |
| 5,916,524 A | 6/1999 | Tisone |
| 6,158,269 A | 12/2000 | Dorenkott et al. |
| 6,526,812 B2 | 3/2003 | Martin et al. |
| 6,669,909 B2 | 12/2003 | Shvets et al. |
| 8,348,844 B2 * | 1/2013 | Kunjan .............. A61B 5/15003 600/366 |
| 2005/0000352 A1 | 1/2005 | Carlsen et al. |
| 2005/0003522 A1 * | 1/2005 | Carlsen .................... B01L 9/52 702/19 |
| 2008/0098828 A1 * | 5/2008 | Li ...................... G01N 35/1097 73/863.73 |
| 2008/0314412 A1 * | 12/2008 | Grippo .................. G01N 30/24 422/400 |

FOREIGN PATENT DOCUMENTS

| | | |
|---|---|---|
| WO | 2007067540 | 6/2007 |
| WO | 2007140015 A2 | 12/2007 |
| WO | 2008051659 | 5/2008 |
| WO | 2008060235 | 5/2008 |
| WO | 2012014050 | 2/2012 |

* cited by examiner

SYSTEM AND APPARATUS FOR FLUID SAMPLE DELIVERY

This United States application is the National Phase of PCT Application No. PCT/NZ2019/050086 filed 24 Jul. 2019, which is based on the provisional specification filed in relation to New Zealand Application No. 744562, the entire contents of which are incorporated herein by reference.

TECHNICAL FIELD

The present disclosure relates to a system and apparatus for fluid sample delivery-more particularly for delivery of a sample having a predetermined volume for analysis using a sensing device.

BACKGROUND

It is common practice in animal husbandry to collect information relating to animals for use in decision making regarding such matters as processing of the milk, culling, breeding, medical treatment, animal specific feed rations as well as measurement of milk production efficiency.

The use of sensors to automatically obtain such information—particularly in relation to milk collected from milking animals—is well known. However, there remain forms of information for which automated sensors are not readily available, or at least have room for improvement in terms of cost efficiency and/or reliability.

More particularly, there are analytes within milk for which it is desirable to use biosensors, due to current challenges in accurate measurements using other sensing mechanisms. A biosensor includes a sensitive bioresponsive element configured to react with at least one analyte in a sample of fluid, with the reaction detected by a detector element, the output of which may be used to measure and quantify the target analyte. Although the use of biosensors is commonplace in laboratory settings, there are challenges to achieving consistent results within a milking environment, particularly when factors such as cost and the need for autonomy are considered.

For example, when aspirating and dispensing individual fluid samples, contamination of both the inside and outside of the sample needle can occur. Excess fluid can remain on the outside of the needle which can decrease the precision of the dosage and can cause problems if the excess liquid subsequently contaminates another liquid sample when the needle is next submerged (termed "carry-over"). In the context of sampling milk, carryover can act to smooth the cow to cow variance—i.e. reduce the accuracy of the analysis. Further, liquids such as milk can include components which are particularly problematic—specifically, the fat content of the liquid also makes the sample want to "stick" to both the inside and outside of the needle. It is also highly important that surfaces exposed to milk are cleaned in order to maintain good hygiene, particularly where the sensor is located within the milking environment, and soiling of the outside of needle can lead to challenges in achieving this.

Another consideration is that issues with inaccuracy can arise from variation in the volume of the sample delivered to the sensitive bioresponsive element. For example, issues with known reaction-pad assays can result from variable sample volumes being placed on the pad, or if an absorbent reaction-pad is allowed to take up a fluid sample by surface wetting, it can tend to overfill (i.e. continue to fill even after complete wetting of the pad has occurred). The overfilling produces a surface film on the pad which may alter the reflectance or absorption characteristics of the pad, and thus skew a surface reading used to determine total analyte-dependent product formed in the reaction. Overfilling can also result in the excess fluid continuing to travel by capillary action and reach other parts of the interior of the device.

It is an object of the present invention to address the foregoing problems or at least to provide the public with a useful choice.

Further aspects and advantages of the present invention will become apparent from the ensuing description which is given by way of example only.

SUMMARY

Exemplary systems, apparatus, and methods are described herein for use in analysing a fluid. In exemplary embodiments, the fluid may be milk extracted from a milking animal. It should be appreciated that while reference will herein be made to a milking animal being a dairy cow this is not intended to be limiting, and the various embodiments of the present disclosure may be used in the milking of other animals, for example: sheep, goats, donkeys, dromedaries, yaks, buffalo, horses and similar. It is envisaged that the present disclosure may have particular application to the analysis of milk during the transfer of milk from the point of extraction to a storage vessel. Milking plants typically include individual milk transport conduits from the points of extraction (for example milking clusters, each of which includes a set of teat cups), joining to a common transport line for delivery to the storage vessel. Samples may be taken from the individual milk transport conduits, or intermediary vessels (such as milk jars), allowing for the analysis of milk extracted from an individual animal before it is combined with milk from other animals. Further, in some embodiments, samples may be taken from milk transport conduits associated with individual teats of an animal, allowing for the analysis of milk from one or more glands of that individual animal.

However, while elements of the present disclosure are described in the context of the analysis of milk extracted from milking animals, it should be appreciated that exemplary embodiments of the present disclosure may have application to use with other fluids, and in other working environments. By way of non-limiting example, it is envisaged that aspects of the present disclosure may have application to environmental monitoring, and liquid processing.

According to one aspect of the present disclosure, there is provided a system for analysing a fluid, including: a sensing element, configured to respond to at least one analyte in a sample of fluid; a detector, configured to sense the response to the analyte by the sensing element; and a fluid sample delivery apparatus, configured to deliver the sample of fluid to the sensing element.

According to one aspect of the present disclosure, there is provided a fluid sample delivery apparatus, including: a dosage needle configured to deliver a sample of fluid to a sensing element; at least one pump configured to control flow of fluid through the dosage needle; and at least one actuator configured to move the dosage needle relative to the sensing element.

According to one aspect of the present disclosure, there is provided a system for analysing a fluid, including: a sensing element configured to respond to at least one analyte in a sample of fluid; a detector configured to sense the response to the analyte by the sensing element; a fluid sample delivery apparatus, the fluid sample delivery apparatus including: a dosage needle configured to deliver the sample of fluid to the sensing element; at least one pump configured to control flow of fluid through the dosage needle; and at least one actuator configured to move the dosage needle relative to the sensing element; and at least one controller configured to control the at least one pump and the at least one actuator.

It is envisaged that exemplary embodiments of the present disclosure may have particular application to biosensors, utilising a sensing element in the form of a bioresponsive element to which the sample is delivered. Aspects of the present disclosure will be discussed herein in the context of biosensors. However, it should be appreciated that aspects of the present disclosure may be used with other types of sensor where it is desirable to deliver a discrete sample of fluid for analysis. For example, the sample may be delivered to a chemically responsive sensing mechanism such as a pH pad, or a nitrate test. By way of further example, it is envisaged that the sample may be delivered to one or more of: a microfluidic system, a lab-on-a-chip, or a capillary tube (which may in turn be used in further processing and analysis of the sample), which may or may not include a bioresponsive element.

It should be appreciated that the bioresponsive element may include any suitable biologically derived material, biomimetic component, or other property that responds to the at least one target analyte (for example, including: tissue, microorganisms, organelles, cell receptors, enzymes, antibodies, nucleic acids, etc) and produces an associated detectable physicochemical response. Similarly, the detector element may be any suitable means for transforming the physicochemical response resulting from the interaction of the analyte with the bioresponsive element (for example: optical, piezoelectric, electrochemical, electrochemiluminescence, etc) into another signal suitable for further processing. The bioresponsive element and detector element may herein be referred to collectively as a "biosensor".

While it will be appreciated that the bioresponsive element may take different forms depending on the nature of the response mechanism, in an exemplary embodiment the bioresponsive element may comprise an absorbent pad (herein referred to as a "single-pad") including dried reagents selected to respond to a target analyte. In an alternative exemplary embodiment the bioresponsive element may be a lateral flow assay, in which the sample migrates along an absorbent strip interacting with a sequence of reagents along the way to generate a measureable response to the target analyte. In an exemplary embodiment, the biosensor platform may be configured to accommodate either or both of single-pad and lateral flow assays.

In an exemplary embodiment, the bioresponsive element may be configured to provide an optically detectable reaction—for example a colorimetric reaction, or a reaction with variable light intensity characteristics. By way of non-limiting example, the biosensor may be configured to: quantify the concentration of beta-hydroxybutyrate in milk, for the purpose of detecting ketosis in dairy animals; or to measure milk urea nitrogen to allow informed decisions to be made about the feed management of dairy animals; or to measure milk lactate concentration for the purpose of detecting mastitis in dairy animals. It will be appreciated that the detector element used will depend on the reaction, and that different forms of detector element may be used. By way of example, a camera may be used to capture colorimetric or other optical reactions. As a further example, one or more photodetectors may be used to detect such reactions.

It is envisaged that the system may be configured to receive a removeable component carrying a plurality of bioresponsive elements, which may be automatically moved into position for receiving the fluid sample. For example, the bioresponsive elements may be provided in the form of pads mounted to a carrier means (such as a flexible strip), the carrier means being moveable to convey the pads into (and away from) the position for receiving the sample. The removable component may include a housing supporting the carrier means, with the carrier means moving the pads between a stored position within the housing and an exposed in-use position. Such an arrangement may be described as a cassette In an exemplary embodiment, the bioresponsive element may remain in the same position through delivery of the sample and subsequent detection of the reaction. However, it should be appreciated that this is not intended to be limiting, as it is contemplated that in an exemplary embodiment the bioresponsive element may be moved from a first location at which the sample is received to a second position at which detection of the reaction is performed.

The term "needle" as used herein is not intended to imply a requirement that the tip of the dosage needle be configured to penetrate a surface—i.e. be sharpened. Rather, it should be appreciated that the term refers to a hollow structure defining a pathway through which fluid may be passed.

It should be appreciated that the at least one actuator configured to move the dosage needle relative to the bioresponsive element may do so in a range of motions and directions, as required by the arrangement of the system, and may be operated by one or more controllers as known in the art.

According to one aspect of the present disclosure, there is provided a method for delivering a sample of fluid to a sensing element of a sensor using a dosage needle, including the steps of: positioning the dosage needle relative to the sensing element such that a gap is provided between at least a portion of an end of the dosage needle from which the sample of fluid is delivered and the sensing element; delivering a predetermined volume of the sample fluid to the sensing element through the dosage needle; and aspirating at least a portion of the sample fluid back from the sensing element.

In an exemplary embodiment, the aspirating may be performed via the dosage needle—although it is also contemplated that in exemplary embodiments a distinct passage may be provided for the aspirating. In an exemplary embodiment, aspiration of the sample fluid from the bioresponsive element may be performed such that an air gap is produced between the tip of the dosage needle and residual sample fluid on the bioresponsive element. It is also envisaged that at least one spacing feature may be provided to physically define the distance between the needle and the sensing element while also being configured to prevent occlusion of the sample of fluid from being delivered to and/or aspirated from the sensing element. In examples of such an embodiment, a gap may be provided without being a complete air gap between the tip of the dosage needle and the residual fluid. In an exemplary embodiment, aspiration may be performed for a predetermined period of time such that air is sucked into the dosage needle.

It is envisaged that this may have particular application to bioresponsive elements for which it is desirable to control one or both of: the volume of sample fluid to be made available for reaction with the bioresponsive element, and the uniformity of distribution of the sample fluid across the bioresponsive element. For example, in the case of a known colorimetric pad the volume of milk absorbed determines the amount of analyte available for reaction with the enzymes. The volume of milk thus will affect the resulting colour reaction and subsequent processing, and may therefore be important to control in order to improve repeatability. The uniformity of application may also determine the amount of analyte available on different areas of the pad, and can lead to non-uniform colour development and therefore loss of accuracy in subsequent processing.

Delivery of the predetermined volume of fluid sample may "flood" the bioresponsive element. It is envisaged by the inventors that the fluid sample may be permitted to mound up over the surface of the bioresponsive element, be held within the edges of the bioresponsive element by natural surface tension, and cover the tip of the needle. Where the bioresponsive element is absorbent, it is believed that this "flooding" process assists with absorption of the necessary amount of sample uniformly across the surface of the bioresponsive element.

In an exemplary embodiment, aspirating of the sample may be initiated after a predetermined period of time following delivery of the sample fluid. It should be appreciated that this time may be influenced by the absorption or response properties of a particular bioresponsive element—but for illustrative purposes is envisaged to be less than five seconds, and more particularly between one to two seconds.

It is envisaged that the duration of aspirating need not be precise, but be sufficient to break the surface tension of the fluid sample covering the surface of the bioresponsive element, and suck air into the dosage needle. After aspirating, the bioresponsive element is left with a thin, uniform layer of sample fluid across its surface.

The inventors consider the thickness of this layer to be dependent on the height of the dosage needle, or at least the inner rim of the bore of the needle, above the bioresponsive element (i.e. the size of the air gap), and that the residual volume may therefore be controlled by this aspect. It should be appreciated that the precise height for a given application may be influenced by the characteristics of the bioresponsive element, the fluid, and the desired residual volume.

The inventors consider that the aspirating of the sample fluid as described may assist with lessening the requirements for precision of the initial volume of sample fluid delivered. This may allow for use of a less-precise, and therefore less costly, pump to be used to perform the delivery and aspiration. For example, peristaltic pumps are considered by the inventors to be well suited to applications handling heterogeneous fluids such as raw unprocessed milk, and relatively reliable and inexpensive—but less precise than other forms of pumps for delivering dosages, such as syringe pumps. However, syringe pumps are considered to be susceptible to blockages due to particulate matter (for example, debris or cells which are relatively common in unprocessed milk), and require more thorough cleaning to maintain operation. Therefore, it is believed that enabling the use of lower-precision pumps may have advantages in terms of one or more of: capital cost, reliability, and ease of cleaning.

In an exemplary embodiment, preparation of the sample of fluid in the dosage needle may be performed prior to positioning the dosage needle above the bioresponsive element.

In an exemplary embodiment a wicking feature may be provided, configured to contact a drop of the fluid suspended from the dosage needle when the needle is in a predetermined position relative to the wicking feature.

Reference to a wicking feature should be understood to mean a structural feature of the system whereby a drop of fluid suspended from the dosage needle coming in contact with that feature is drawn away from the needle. In an exemplary embodiment the wicking feature may be an upright wall as described further below, however alternative forms are expressly contemplated. For example, the wicking feature may include an upright elongate protrusion such as a pin or a shaft. It is envisaged that such features may provide sufficient surface area to negate the adhesion of the drop to the needle, and allow gravity to take the drop away. While an absorbent wicking material may provide a similar effect, it is envisaged that a non-porous feature may assist with ease of cleaning of the system.

According to one aspect of the present disclosure, there is provided a method for preparing a sample of fluid in a dosage needle prior to delivery to a sensing element of a sensor, including the step of: positioning a tip of the dosage needle proximate to a wicking feature, such that a drop of the fluid formed on the tip is wicked away from the dosage needle by the wicking feature.

In an exemplary embodiment, the system may include a chamber having an upper wall, the upper wall having an aperture configured to receive the dosage needle.

In an exemplary embodiment, the wicking feature may be provided in an interior of the chamber.

According to one aspect of the present disclosure, there is provided a chamber for use with a fluid sample delivery apparatus having a dosage needle configured to deliver a sample of fluid, the chamber including: a wicking feature provided in an interior of the chamber; and an upper wall having an aperture configured to receive the dosage needle such that a tip of the dosage needle is proximate to the wicking feature, such that a drop of the fluid formed on the tip is wicked away from the dosage needle by the wicking feature.

According to one aspect of the present disclosure, there is provided a system for analysing a fluid substantially as herein described, including a chamber substantially as herein described.

According to one aspect of the present disclosure, there is provided a fluid sample delivery apparatus substantially as herein described, including a chamber substantially as herein described.

In an exemplary embodiment, the wicking feature may be an upright wall of the chamber.

Reference to the wicking feature, and more particularly the wall of the chamber, being upright should be understood to mean a generally vertical orientation relative to ground, such that fluid in contact with the upright surface of the wicking feature drains downwardly. In an exemplary embodiment the wicking element may be non-vertical—i.e. not 90° relative to an imaginary horizontal plane parallel to ground—while remaining upright. It is envisaged that this may assist with reducing the likelihood of the sample fluid tracking up the sides of the dosage needle. In an exemplary embodiment the slope of the wicking element may be between 50° to 80° relative to a horizontal plane parallel to ground, for example about 60°, but it should be appreciated that this is not intended to be limiting to all embodiments.

In an exemplary embodiment, the tip of the needle may be laterally spaced from the wicking feature. It is envisaged that the resulting gap may be such that a drop of the sample fluid forming or formed on the tip of the dosage needle contacts the upright wall and is wicked away. As the fluid exits the needle, it forms an oblong drop due to surface tension, and grows in volume until the force of gravity on the mass of the drop is enough to break the adhesion to the needle. The positioning of the dosage needle relative to the wicking feature may be such that the drop makes contact with the wicking feature before gravity releases it from the needle.

The volume of a drop may be significant in comparison with the volume of the sample to be delivered to the bioresponsive element—for example, a sample volume in the order of microlitres (for example, 3 to 5 μL), in comparison with a drop being in the order of 50 μL. It is believed that the wicking action assists in achieving a consistent volume of sample fluid within the dosage needle, which in turn assists with repeatability of the volume delivered to the bioresponsive element and therefore the repeatability of the measurements obtained by the biosensor. The ability to remove such drops prior to delivery of the sample may also assist with the use of lower precision pumping mechanisms—for example, a peristaltic pump—while maintaining an acceptable level of accuracy. It is also envisaged that by removing drops from the end of the dosage needle before transportation to the bioresponsive element, the likelihood of drops being dislodged and contaminating other areas of the system may be reduced.

It should be appreciated that the dimensions of this lateral spacing may be influenced by factors such as the dimensions of the tip of the needle, which in turn influence the size of any drop formed on the tip. Further, properties of the fluid itself will influence behaviours such as the formation of drops and adhesion. It is believed that if the distance is too great, a drop may be released from the needle tip before making contact with the wicking feature surface—while if the distance is too low, the fluid may form a bridge between the needle and wall, and leave excess fluid on the outside of the needle. However, by way of example, the inventors have determined that for a needle size of 15 gauge (1.82 mm outer diameter×1.35 mm inner diameter, stainless steel 304, supplied by Coopers Needle Works Limited), the optimum gap may be in the order of 1.0±0.3 mm.

In exemplary embodiments, the tip of the dosage needle may be positioned to be at least flush with at least a portion of an inner surface of the upper wall facing into the interior of the chamber. In exemplary embodiments the dosage needle may project into the chamber beyond the inner surface of the upper wall.

In an exemplary embodiment, a drop may be formed on the tip of the dosage needle prior to insertion into the chamber. It is envisaged that this may assist with the formation of a drop of sufficient volume to be wicked away within the chamber, but with a reduced likelihood of sample fluid within the needle being drawn out during the wicking action, along with the drop itself.

In an exemplary embodiment, the inner surface of the upper wall may be sloped. More particularly, the upper wall may be sloped downwardly towards the wicking feature, more particularly the upright wall. It is envisaged that this may assist with the draining of any fluid contacting the upper wall, down towards the bottom of the chamber. Further, this may assist with reducing the likelihood of air becoming entrapped around the tip of the dosage needle when the chamber is filled with a cleaning fluid-rather than exposing the tip of the dosage needle to the cleaning fluid. It is envisaged that the slope of the upper wall may be less than 10° relative to a horizontal plane parallel to ground, for example about 5°, but it should be appreciated that this is not intended to be limiting to all embodiments.

In an exemplary embodiment, the chamber may include a waste port. It is envisaged that the waste port may be positioned at a lowermost point in the chamber. In an exemplary embodiment a waste pump may be provided to the waste port.

In an exemplary embodiment, the chamber may include an overflow port. In an exemplary embodiment the overflow port may be positioned distal from the upright wall, and above the aperture in the upper wall. In doing so, the chamber may be filled with cleaning fluid such that the tip of the dosage needle is immersed in the cleaning fluid for cleaning, before reaching the overflow port. In an exemplary embodiment, the overflow port may be positioned in the uppermost point in the chamber, to ensure contact between the entire chamber and the cleaning fluid.

In an exemplary embodiment, an overflow valve may be provided at the overflow port to prevent backflow into the chamber through the overflow port. It is envisaged that the overflow valve may be a check valve, for example a duckbill type valve. In an exemplary embodiment in which a waste pump is provided to the waste port, the overflow port may be connected downstream of the waste pump, with the overflow valve preventing the backflow of waste through the overflow port. In an exemplary embodiment, the overflow valve may be provided at the overflow port. It is envisaged that doing so may reduce or avoid headspace within tubing from the overflow port, from which bubbles may be produced at undesired times.

In an exemplary embodiment, an air bleed valve may be provided in the chamber, configured to permit inflow of air to ensure pressure equalisation. In an exemplary embodiment, the air bleed valve may be a duckbill type valve. In an exemplary embodiment, the air bleed valve may be provided in a substantially central location in the chamber. For example, the chamber may include a side wall adjoining the upper wall and upright wall, with the air bleed valve located in a substantially central location on the side wall.

In an exemplary embodiment, the waste pump may be operated while cleaning fluid is within the chamber, to create a pressure differential such that air is introduced through the air bleed valve. It is envisaged that this air may produce turbulence within the chamber to assist with cleaning.

In an exemplary embodiment, cleaning fluid may be introduced to the chamber through the dosage needle. For example, it is envisaged that the source of the sample fluid—for example, transfer lines of a milking plant—will be subject to a cleaning cycle in which cleaning fluid is passed through the source. During such a cleaning cycle, the cleaning fluid may be extracted using the same mechanism used to extract the sample, and used to clean components of the system, and in particular the fluid sample delivery apparatus. However, it should be appreciated that this is not intended to be limiting to all embodiments, and that a dedicated supply of cleaning fluid may be provided for this purpose.

In an exemplary embodiment the chamber may include: a waste port positioned at a lowermost point in the chamber; a waste pump provided to the waste port; an overflow port positioned above the aperture in the upper wall; and an overflow valve provided to the overflow port to prevent backflow into the chamber through the overflow port.

According to one aspect of the present disclosure, there is provided a dosage needle, including a barrel portion having a tip from which a sample of fluid is delivered.

It should be appreciated that dimensions of the dosage needle, for example inner diameter, may be influenced by characteristics of the sample to be delivered. For example, where the volume of the sample is in the order of microlitres (for example, 3 to 5 μL), the inner diameter of the needle may be in the order of 1.0 to 1.5 mm to assist with allowing for a relatively long pump stroke while still achieving an acceptable level of precision.

In an exemplary embodiment, the dosage needle may include a barrel portion leading to the tip. In an exemplary embodiment, a seal may be provided on the exterior of the barrel portion. The seal may be configured to seal against the aperture in the upper wall. It is envisaged that such an arrangement may be preferred to one in which the needle is inserted through a seal affixed to the aperture, which may create difficulties in cleaning residual fluid from the exterior of the needle.

In an exemplary embodiment, the tip end of the barrel portion may extend beyond the seal. It is envisaged that this may assist with reducing the likelihood of residual sample fluid tracking up to the seal. It should be appreciated that in such an embodiment, the distance by which the tip extends from the seal may be influenced by factors such as the dimensions of the tip of the needle, which in turn influence the size of any drop formed on the tip. Further, properties of the fluid itself will influence behaviours such as adhesion and tracking along the exterior of the needle.

However, it is also expressly contemplated that the seal may extend to the tip of the dosage needle. In such an embodiment, the tip of the seal may effectively extend the surface area of the tip of the dosage needle. It is envisaged that this may be leveraged to provide a wide area of coverage of the bioresponsive element to which the sample is to be delivered. Further, the wide area may influence production of a large drop for wicking purposes.

In an exemplary embodiment, the tip of the dosage needle may be bevelled. It is envisaged that this may reduce the likelihood of the sample fluid tracking up the exterior of the needle.

In an exemplary embodiment in which the seal extends to the tip of the dosage needle, at least a portion of the exterior of the seal may be tapered towards the tip. It is envisaged that this may increase the positional tolerance for successful docking with the chamber, making it easier to dock the needle. This may be achieved, for example, by shaping of the exterior of the seal itself, or by the shape of the dosage needle beneath the seal (such as a barb at the tip).

In an exemplary embodiment, the docking aperture may be tapered towards the interior of the chamber. In an exemplary embodiment, the angle of the taper of the docking aperture may be greater than a taper on the exterior of the needle, or the seal. In doing so, the sealing interface is at the inner face of the upper wall rather than within the aperture, avoiding creation of a gap in which soiling might otherwise occur.

The exemplary system(s) including the bioresponsive element and associated detector may herein be referred to as a biosensor, or sensor. Various configurations of sensors, in terms of how the sensor is exposed to the fluid to be analysed, are known in the art. Terms such as "in-line", "on-line", "at-line", "near-line" and "off-line" are used in the art to distinguish between these configurations—however there is a degree of inconsistency in their usage. Reference will be made herein to "in-line", "on-line", "off-line", and "sample" sensors, which for clarity may be defined as follows.

Reference herein to an in-line sensor should be understood to mean a sensor analysing fluid flowing past one or more sensing means, to determine at least one parameter of the fluid at a particular point or period of time—i.e. without collection of a discrete sample from the flow.

Reference to an on-line sensor should be understood to mean a sensor which automatically extracts a sample of fluid from a fluid source, and analyses the sample of fluid to determine at least one parameter of the sample. As used herein, the term "on-line" may encompass embodiments in which the sample is returned to the fluid source, or discarded.

The terms "at-line" and "off-line" may be used in the art to distinguish between the environment in which the sensor is configured to operate. Both at-line and off-line sensors are configured to analyse a discrete sample of the fluid delivered to the sensor by an operator. At-line sensors (which may be referred to as "near-line" sensors) are generally intended to be located within the vicinity of the fluid flow—for example, within a milking facility—while off-line sensors are primarily intended for use in a more environmentally controlled environment—for example, in a laboratory. In practice, particularly for milking operations, analysis of a sample by an off-line sensor may necessitate transport of the sample from the sample source to a remote facility. As used herein, the term "off-line" should be understood to refer to a sensor configuration in which a sample is collected from the fluid, and delivered to the sensor by an operator rather than an automated system.

On-line and off-line sensors, as defined herein, may be distinguished from in-line sensors by the act of analysing a sample extracted from the fluid rather than analysing the flow of fluid itself. As such, on-line and off-line sensors may be referred to in the collective as "sample" sensors.

In exemplary embodiments, the system(s) of the present disclosure may be configured to extract a sample of the fluid from a fluid source using a sample extraction device—i.e. may relate to on-line sensors. As such, the system may include a sample extraction device configured to extract the sample, and a sensing device configured to receive and analyse the sample (e.g. having the bioresponsive element, detector, and fluid sample delivery apparatus). It should be appreciated that in exemplary embodiments the components of the sample extraction device and sensing device may be realised in a single unit, while in others they may be separated.

The system may include extraction means—for example one or more pumps, such as peristaltic pumps—to draw fluid from the fluid source, and deliver it to the sensing device. For completeness, it will be appreciated that operation of the pumps of the system may be controlled by one or more controllers.

Other features of the technology will be apparent from consideration of the information contained in the following detailed description, and drawings.

BRIEF DESCRIPTION OF DRAWINGS

Further aspects of the present invention will become apparent from the following description which is given by way of example only and with reference to the accompanying drawings in which:

FIG. 1 is a schematic diagram of an exemplary livestock management system in which an aspect of the present disclosure may be implemented;

FIG. 2 is a schematic diagram of an exemplary sensor system according to one aspect of the present disclosure;

FIG. 3A is a perspective view of an exemplary chamber for use in the sensor system;

FIG. 3B is a side view of a portion of the exemplary chamber;

FIG. 3C is an end cross-section view of a portion of the exemplary chamber;

FIG. 4A-C are side cross-section views of a dosage needle illustrating different filling conditions;

FIG. 5 is a side view of an exemplary dosage needle for use in the sensor system;

Figure 13A:
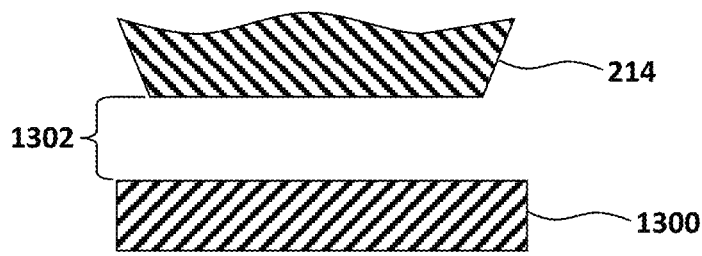
Figure 13B:
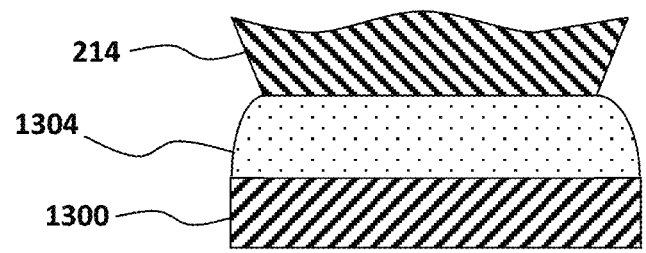
Figure 13C:
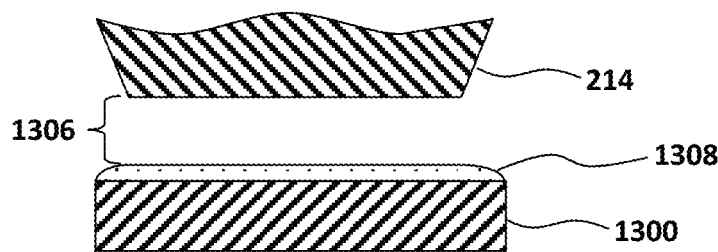
Figure 14A:
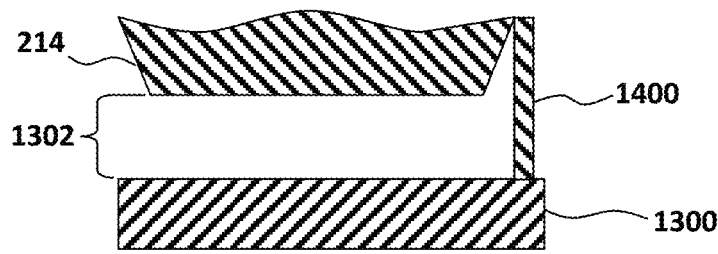
Figure 14B:
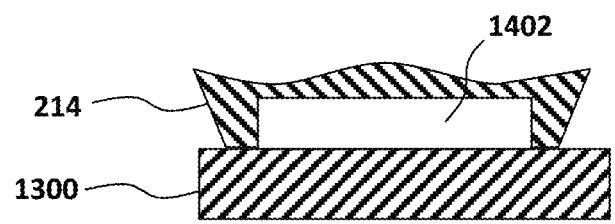
Figure 14C:
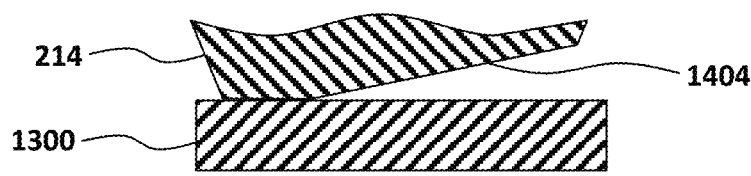
Figure 15:
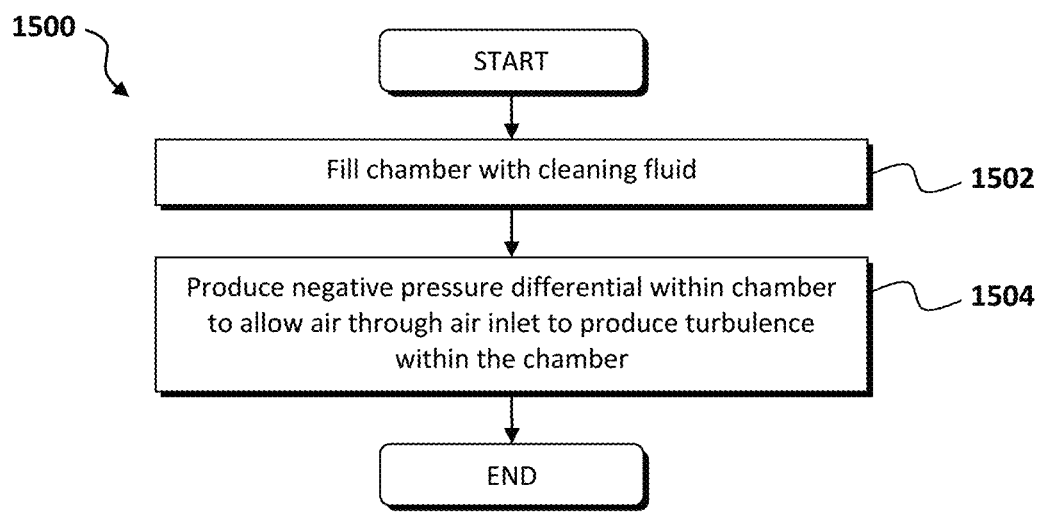

FIG. 13A-C illustrate the tip of a dosage needle relative to a bioresponsive element during delivery of a sample of fluid;

FIG. 14A-C illustrate examples of dosage needles including at least one spacing feature; and FIG. 15 is a flow diagram of a method of cleaning a dosage needle and sample chamber in place.

DETAILED DESCRIPTION

Exemplary embodiments are discussed herein in the context of analysis of milk. However, it should be appreciated that the various systems, apparatus and methods of the disclosure discussed herein may be applied to the analysis of other fluids.

Figure 1:
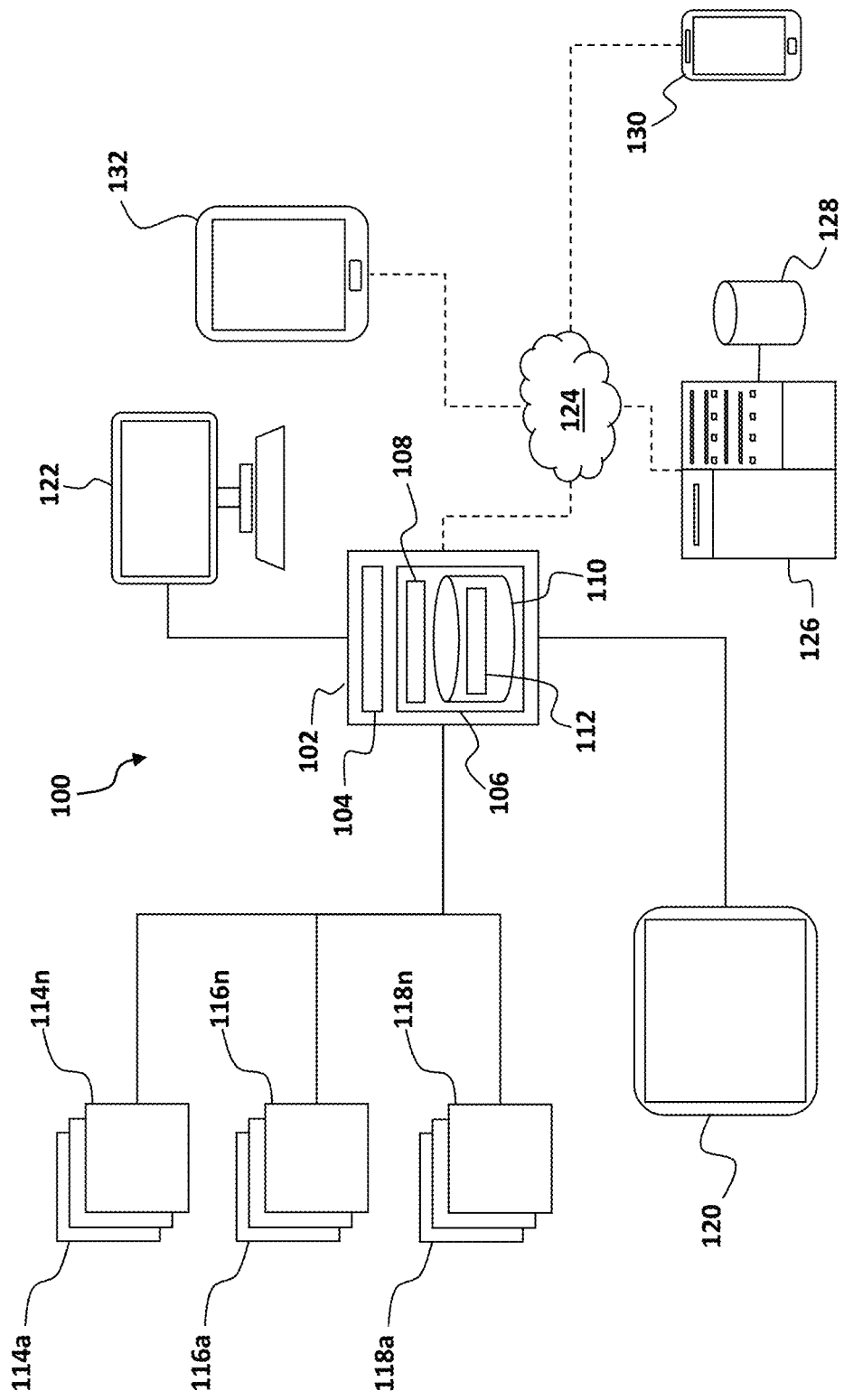

FIG. 1 illustrates a livestock management system 100, within which a local hardware platform 102 manages the collection and transmission of data relating to operation of a milking facility. The hardware platform 102 has a processor 104, memory 106, and other components typically present in such computing devices. In the exemplary embodiment illustrated the memory 106 stores information accessible by processor 104, the information including instructions 108 that may be executed by the processor 104 and data 110 that may be retrieved, manipulated or stored by the processor 104. The memory 106 may be of any suitable means known in the art, capable of storing information in a manner accessible by the processor 104, including a computer-readable medium, or other medium that stores data that may be read with the aid of an electronic device. The processor 104 may be any suitable device known to a person skilled in the art. Although the processor 104 and memory 106 are illustrated as being within a single unit, it should be appreciated that this is not intended to be limiting, and that the functionality of each as herein described may be performed by multiple processors and memories, that may or may not be remote from each other. The instructions 108 may include any set of instructions suitable for execution by the processor 104. For example, the instructions 108 may be stored as computer code on the computer-readable medium. The instructions may be stored in any suitable computer language or format. Data 110 may be retrieved, stored or modified by processor 104 in accordance with the instructions 110. The data 110 may also be formatted in any suitable computer readable format. Again, while the data is illustrated as being contained at a single location, it should be appreciated that this is not intended to be limiting—the data may be stored in multiple memories or locations. The data 110 may also include a record 112 of control routines for aspects of the system 100.

The hardware platform 102 may communicate with various devices associated with the milking facility, for example: in-line sensors 114a to 114n associated with individual milking clusters within the milking facility, and sample sensors in the form of on-line sensors 116a to 116n associated with the individual milking clusters.

Animal identification devices 118a to 118n are provided for determining an animal identification ("animal ID") of individual animals entering, or within, the milking facility. More particularly, the animal identification devices 118a to 118n may be used to associate an animal ID with each of the milking clusters associated with the in-line sensors 114a to 114n and on-line sensors 116a to 116n, such that the sensor data may be attributed to the individual animals. A variety of methodologies are known for the determination of an animal ID—for example a radio frequency identification ("RFID") reader configured to read a RFID tag carried by the animal. In an alternative embodiment, or in conjunction with the animal identification devices 118a to 118n, a user may manually enter (or correct) animal IDs via a user device—examples of which are discussed below.

The hardware platform 102 may also communicate with user devices, such as touchscreen 120 located within the milking facility for monitoring operation of the system, and a local workstation 122. The hardware platform 102 may also communicate over a network 124 with one or more server devices 126 having associated memory 128 for the storage and processing of data collected by the local hardware platform 102. It should be appreciated that the server 126 and memory 128 may take any suitable form known in the art—for example a "cloud-based" distributed server architecture. The network 124 potentially comprises various configurations and protocols including the Internet, intranets, virtual private networks, wide area networks, local networks, private networks using communication protocols proprietary to one or more companies-whether wired or wireless, or a combination thereof. It should be appreciated that the network 124 illustrated may include distinct networks and/or connections: for example, a local network over which the user interface may be accessed within the vicinity of the milking facility, and an internet connection via which the cloud server is accessed. Information regarding operation of the system 100 may be communicated to user devices such as a smart phone 130 or a tablet computer 132 over the network 124.

Figure 2:
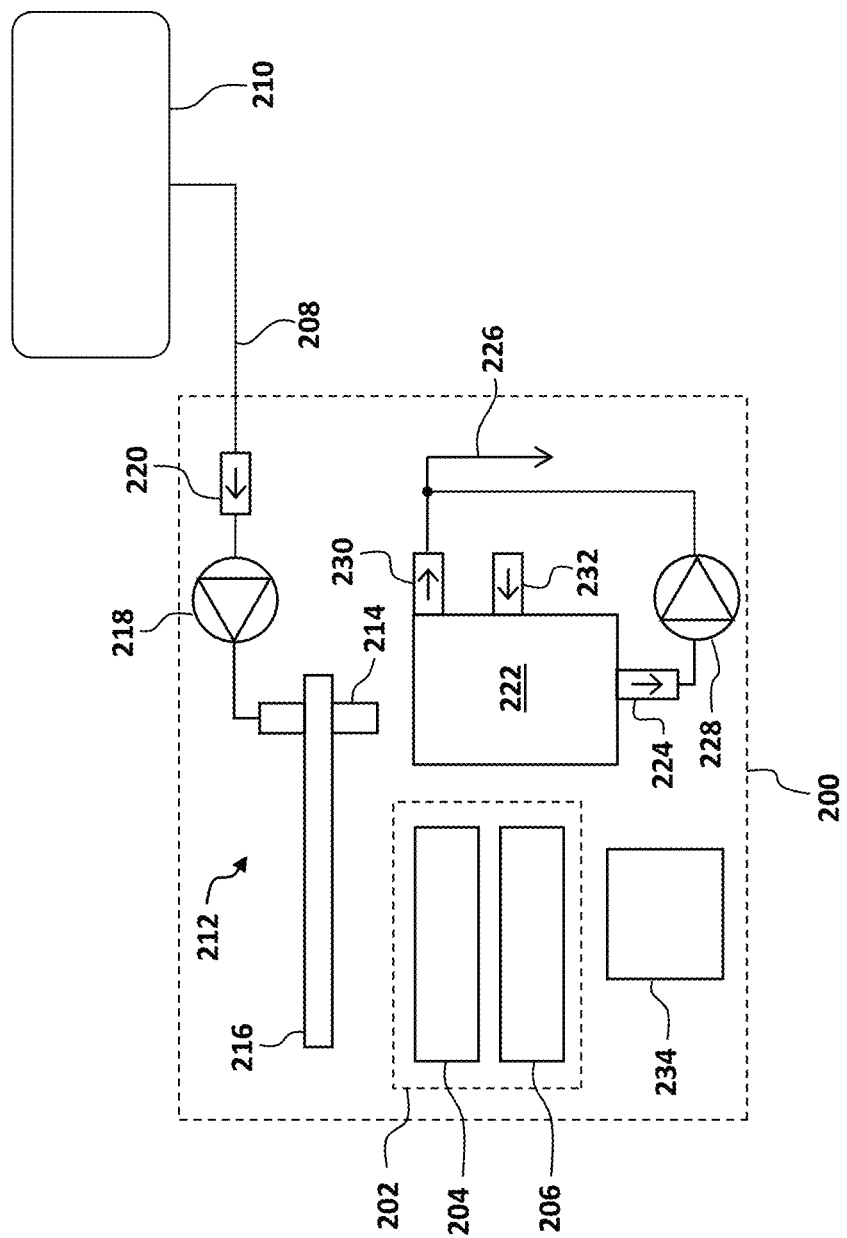

Referring to FIG. 2, an exemplary sensor 200 is illustrated, which may be used as one or more of the on-line sensors 116a to 116n. In this exemplary embodiment, the on-line sensor 200 includes a biosensor 202 having a bioresponsive element 204 and a detector 206, configured to sense interaction of an analyte within a milk sample with the biosensor element. For example, the biosensor 202 may be a colorimetric sensor having a camera configured to capture the colour of a reaction-pad assay. Various colorimetric based tests are known in the field of animal health and milk quality, for example detecting lactate, beta-hydroxybutyrate (BHB), and urea.

A sample delivery tube 208 is connected near or at the bottom of a source of the fluid to be sampled—for example milk jar 210—and connects the milk jar to a fluid delivery apparatus (generally indicated by arrow 212). The fluid delivery apparatus 212 includes a dosage needle 214 mounted to needle actuator 216, configured to manipulate the position of the dosage needle 214 relative to associated components of the sensor 200. A first peristaltic pump (herein referred to as sensor pump 218) is provided to control flow of milk through the dosage needle 214 from the milk jar 210, with a first non-return valve 220 preventing flow of milk back through the sample delivery tube 208.

A sample chamber 222 is provided for preparation of the dosage needle 214 prior to delivery to the biosensor 202, and subsequent cleaning. A waste outlet is provided with a valve in the form of first duckbill valve 224, connected to waste 226 via a sample waste pump 228. An overflow port is provided with an overflow valve in the form of a check valve (more particularly, in the form of a second duckbill valve 230), connected to waste 226 downstream of the sample waste pump 228. An air bleed valve in the form of third duckbill valve 232 is provided between the chamber 222 and atmosphere.

A controller 234 is provided to control the operation of the various components described, receive data obtained by the biosensor 202, and communicate over a network such as the network 124.

Figure 3A:
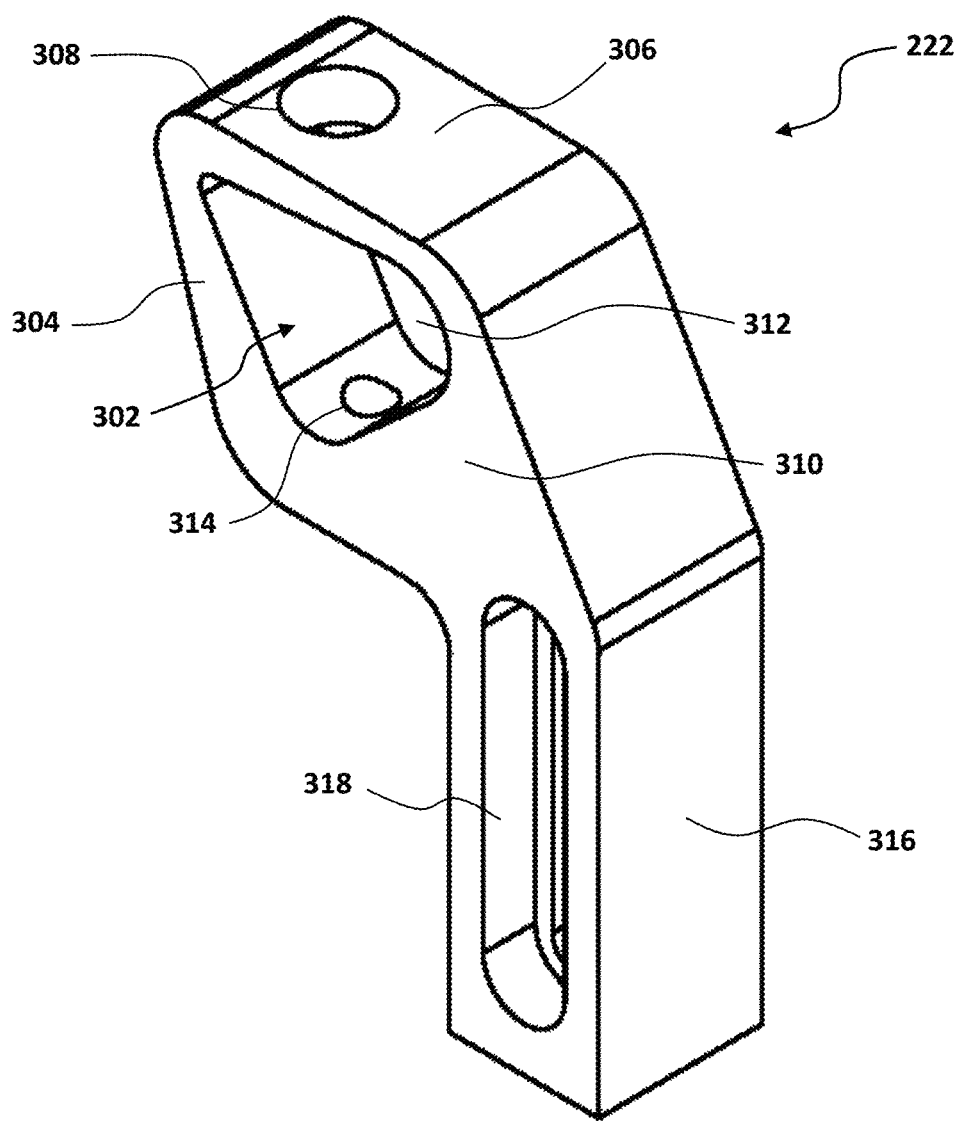
Figure 3B:
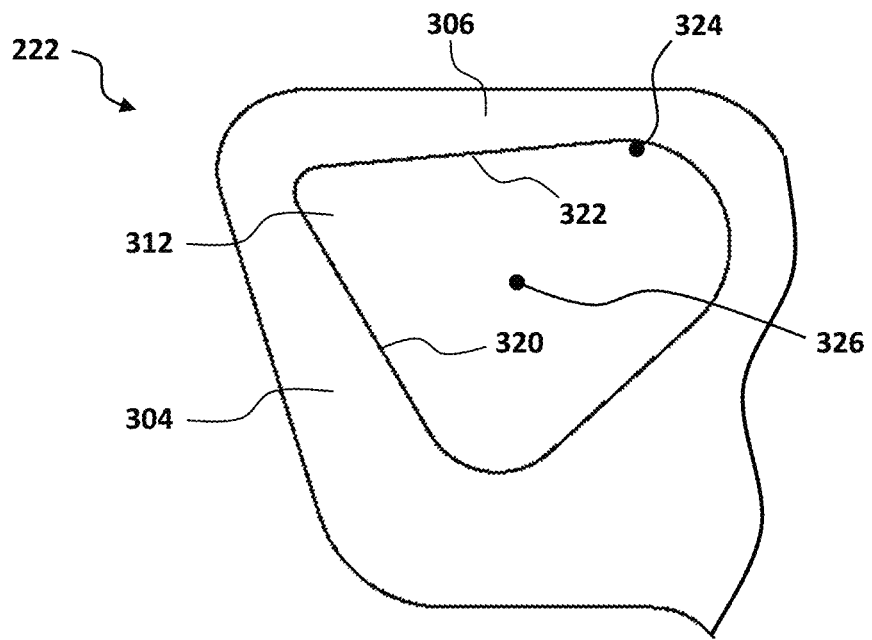
Figure 3C:
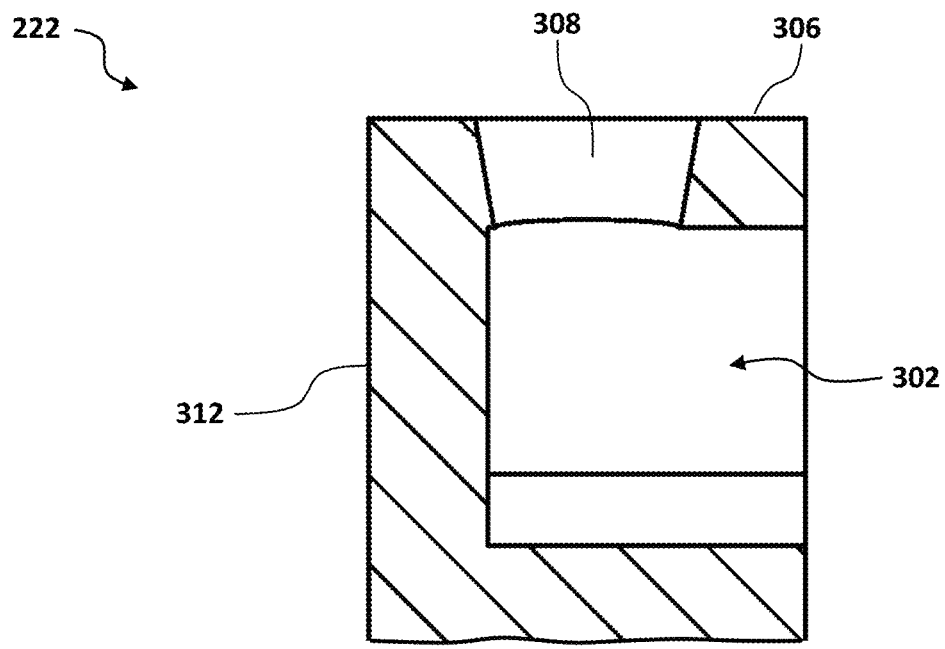

FIG. 3A to 3C illustrate an exemplary embodiment of the sample chamber 222, in the form of sample chamber 222. The sample chamber 222 includes a hollow chamber 302. The hollow chamber 302 is defined by an upright wall 304, upper wall 306 (having a dosage needle aperture 308), second wall 310, rear wall 312, and a front wall (not illustrated, but spanning the hollow chamber 302 opposite the rear wall 312). A waste port 314 is provided at the nadir of the hollow chamber 302, to which the first duckbill valve 224 of FIG. 2 may be provided. In the exemplary embodiment illustrated, the sample chamber 222 includes an adjustment member 316 having an elongate slot 318 which may be used to adjust the position of the sample chamber 222 (particularly height) relative to a reference point.

Referring to FIG. 3B, the upright wall 304 of sample chamber 222 includes an upright inner surface 320 facing into the hollow chamber. In the exemplary embodiment illustrated, the angle of the upright inner surface 320 relative to ground is substantially 60°. The upper wall 306 of sample chamber 222 includes a downward facing inner surface 322 facing into the hollow chamber. In the exemplary embodiment illustrated, the angle of the downward facing inner surface 322 relative to ground is substantially 5°, sloping downwardly towards the upright wall 304.

While not illustrated, an overflow port may be provided at position 324 (herein referred to as "outlet port 324" for ease of understanding), in either the rear wall 312 or front wall (not illustrated). The overflow port 324 is provided above the dosage needle aperture 308 (not illustrated in FIG. 3B, but see FIG. 3A), such that when the hollow chamber is filled with a fluid, the tip of a dosage needle inserted through the dosage needle aperture 308 is covered by the fluid before reaching the overflow port 324. The second duckbill valve 230 of FIG. 2 may be provided at overflow port 324. An air inlet may be provided at position 326 (herein referred to as "air inlet 326" for ease of understanding), in either the rear wall 312 or front wall (not illustrated). The third duckbill valve 232 of FIG. 2 may be provided at air inlet 326.

Figure 4A:
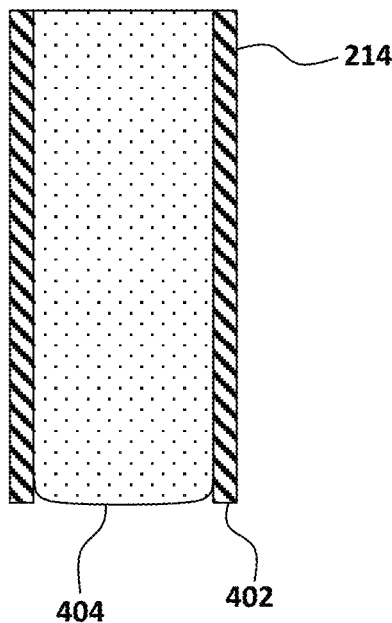
Figure 4B:
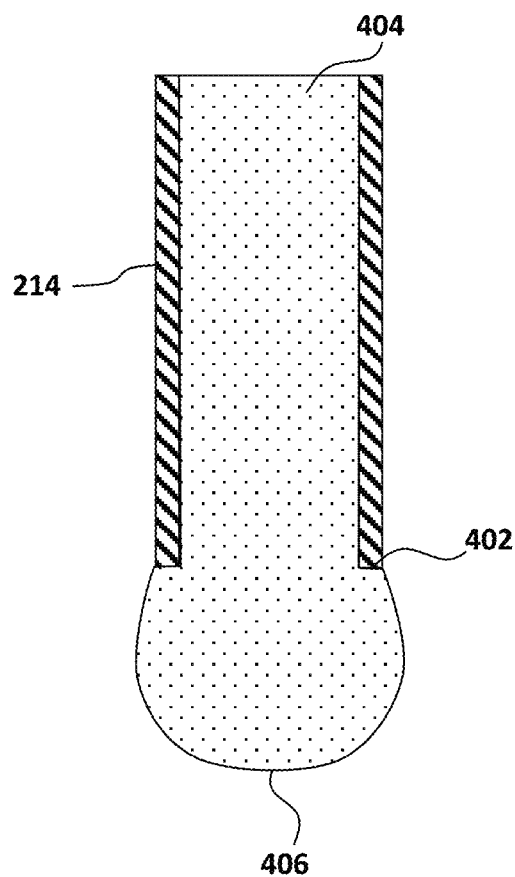
Figure 4C:
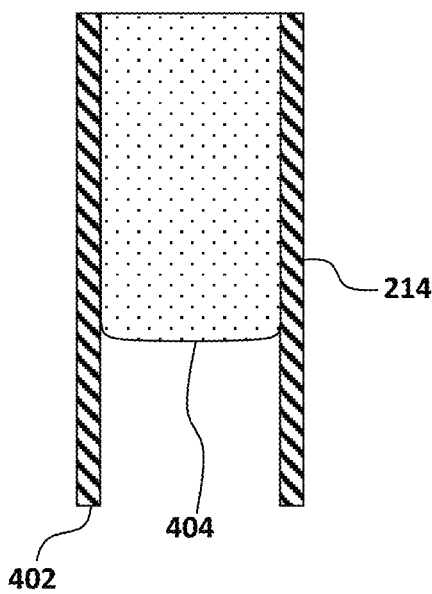

Variation in the volume of fluid delivered through a dosage needle may be influenced by the filling of the needle prior to delivery—particularly relative to the needle tip. FIG. 4A illustrates a preferred condition, in which a dosage needle 214 having tip 402 is filled with the sample fluid 404 such that it is flush with the tip 402. However, it has been observed that with relatively small internal diameters of a needle (for example, in the order of 1.3 mm), relatively low flow rates, and surface tension of the sample fluid, the sample fluid exits the needle as a series of droplets when suspended in open air. As a result, and with reference to FIG. 4B, a drop 406 of various volumes may be produced at the tip 402 of the needle 400 once the flow of sample fluid 404 has stopped (for example, depending on where an associated pump finishes in relation to the fluid flow). Excess drops 406 may be generally undesirable because they can have a volume (for example, 50 µL) that is significant in comparison with the volume to be applied to the sensor (for example 3 to 5 µL), potentially causing large variations and a reduction in repeatability. Excess drops 406 also have a risk of being knocked off during needle movement, thereby causing soiling of components within the system. As shown in FIG. 4C, if the needle 214 is underfilled (whether by stopping pumping of the fluid 404 short of the needle tip 402, or by a falling drop drawing additional fluid with it) the volume of the sample may be undersized.

Figure 5:
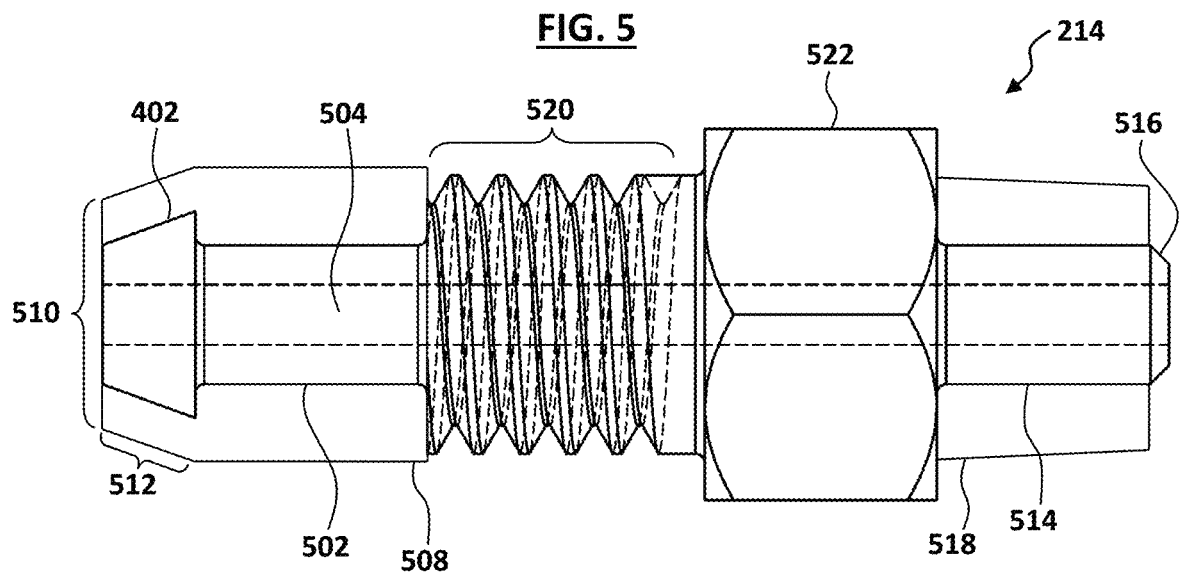

FIG. 5 illustrates an exemplary dosage needle 214. A needle barrel 502 includes a bore 504 (for example, having an internal diameter of about 1.3 mm), having a barbed tip 402. A seal in the form of a silicone sleeve 508 is positioned on the needle barrel 502 such that the end of the sleeve 508 is flush with that of the barbed tip 402, to present a tip surface 510. The barbed tip 402 produces a taper 512 on the exterior of the sleeve 508 at the tip end.

In use, the distal end of the needle 214 from the tip 402 will be connected to a sample delivery tube. However, for illustrative purposes, in FIG. 5 a second configuration of a dosage needle tip and seal is shown. In the second configuration, a straight needle barrel 514 terminates in a bevelled tip 516. A seal in the form of a silicone bung 518 is positioned on the straight needle barrel 514, such that the bevelled tip 516 projects beyond the silicone bung 518.

In the exemplary embodiment illustrated, the dosage needle 214 includes means for adjusting the height of the dosage needle relative to other components in the system-more particular an external thread portion 520 configured to engage with a threaded bore of a needle carrier (for example, of fluid delivery apparatus 212), and a tool engaging portion 522 for rotation of the dosage needle 214 to carry out the height adjustment.

Figure 6A:
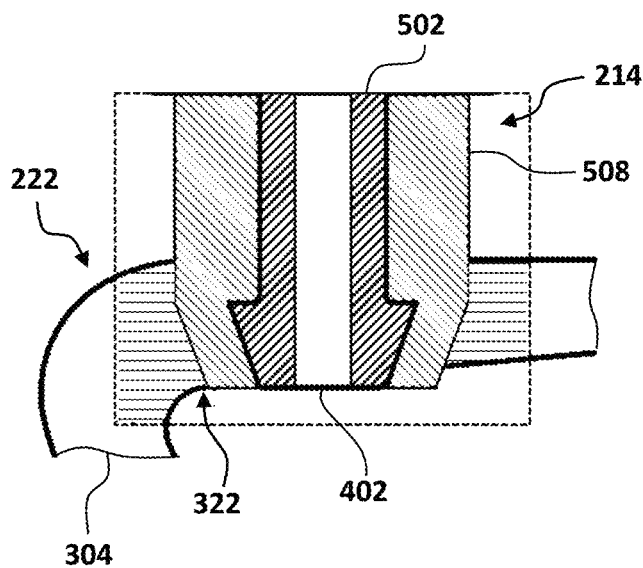
FIG. 6A is a side cross-section view of an exemplary dosage needle engaged in an exemplary chamber.

FIG. 6A illustrates an exemplary relationship between a sample chamber 222 and a dosage needle 214 having a needle barrel 502 surrounded by silicone sleeve 508. The dosage needle 214 is inserted through a dosage needle aperture in the chamber 222, such that a tip 402 of the needle 214 closest to the upright wall 304 is at least flush with the inner surface 322 of the upper wall of the chamber 222 and preferably projecting into the chamber.

Figure 6B:
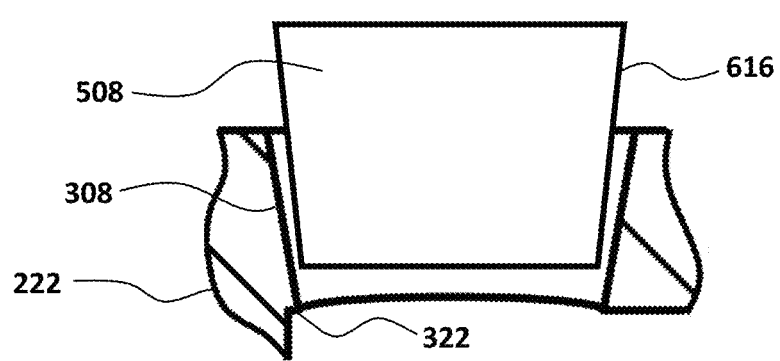
FIG. 6B is a side cross-section view of the exemplary dosage needle and chamber.

Referring to FIG. 6B, the dosage needle aperture 308 is tapered towards the interior of the chamber 222. The angle of the taper of the dosage needle aperture is greater than the taper on the exterior 616 of the sleeve 508, such that the sealing interface occurs at the inner surface 322 rather than recessed within the aperture 308.

Figure 7:
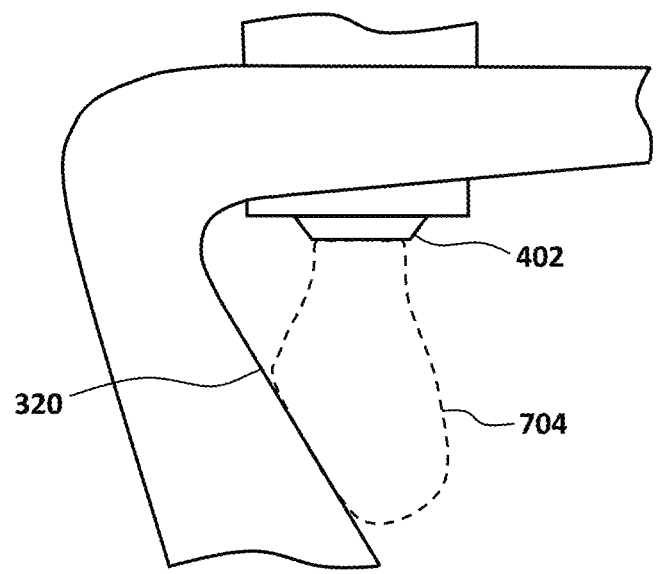
FIG. 7 is a side view of an exemplary dosage needle engaged in an exemplary chamber, illustrating wicking of sample fluid from the needle.

Referring to FIG. 7, the inner surface 320 of the upright wall of the chamber is sufficiently close to the tip 402 of the dosage needle (when inserted into the chamber) such that a drop 704 of sample fluid forming on the tip 402 contacts the inner surface 320 of the upright wall. As the drop 704 grows in volume, the force of gravity on the mass of the drop 704 is enough to break the adhesion to the tip 402. The drop 704 needs to make contact with the inner surface 320 before gravity releases it from the tip 402, so that surface tension is broken and the fluid is gently wicked away-rather than drawing additional fluid to result in the underfilled state shown in FIG. 4C.

Figure 8:
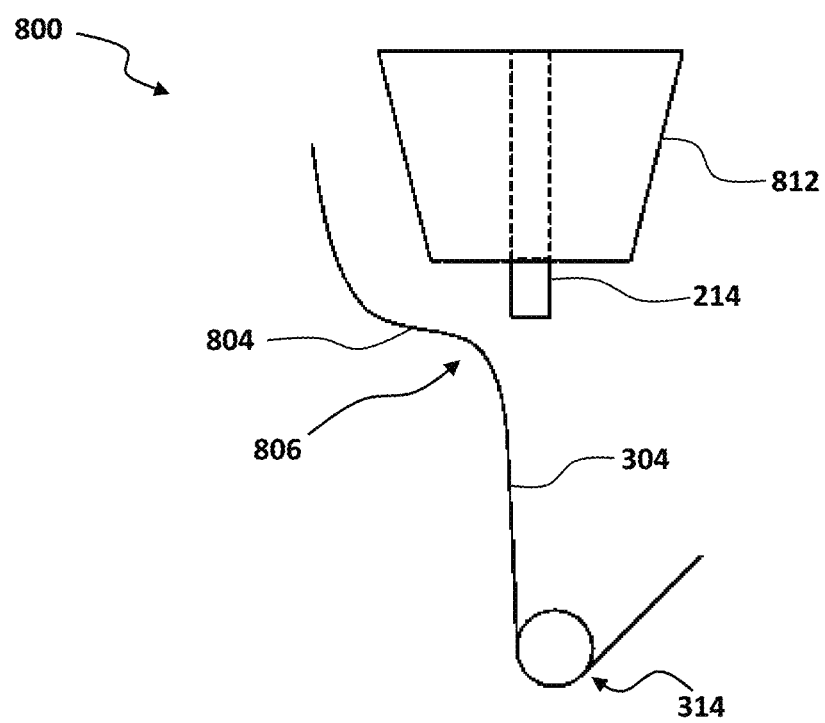
FIG. 8 is a side view of another exemplary configuration of a dosage needle and chamber.

FIG. 8 illustrates an alternative embodiment of the interior 800 of the sample chamber, having an upright wall portion 304 and a sloped ledge 804, with a curved corner 806 therebetween, and a waste port 314 at the base of the upright wall 304. The sloped ledge 804 accommodates an arrangement in which a narrow needle 214 is surrounded by a sealing bung 812 having a substantially greater diameter. In the exemplary embodiment illustrated, the needle 214 projects beyond the bung 812. It is envisaged that for embodiments in which the needle 214 is thin walled, and therefore cannot easily accommodate measures such as a bevelled or tapered tip, this extension may assist with reducing the likelihood of sample fluid tracking up the exterior of the bung 812 to a point where it will not be cleaned.

Figure 9:
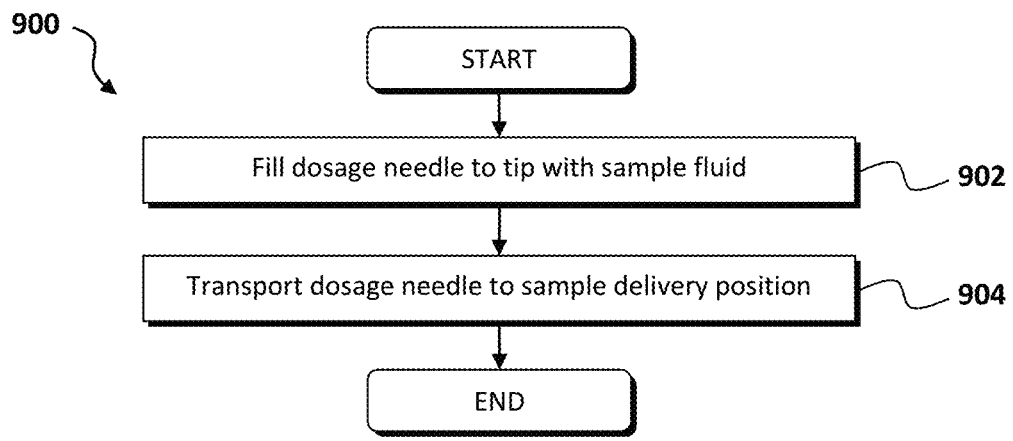
FIG. 9 is a flow diagram of a method of preparing a dosage needle for delivery of a sample of fluid to a sensing element.

FIG. 9 illustrates a method 900 of preparing a dosage needle (for example, dosage needle 214) for delivery of a sample of fluid to a sensing element (for example, bioresponsive element 204 of biosensor 202). In a first step 902, the needle 214 is filled to its tip with the sample fluid—for example, as illustrated in FIG. 4A. In an exemplary embodiment this may be achieved by: forming a drop at the tip of the dosage needle 214, such that it contacts an upright wall (for example, the upright inner surface 320 of upright wall 304 of sample chamber 222) and is wicked away by the upright wall. In a second step 904 the dosage needle 214 is transported to a sample delivery position—for example, above the bioresponsive element 204.

Figure 10:
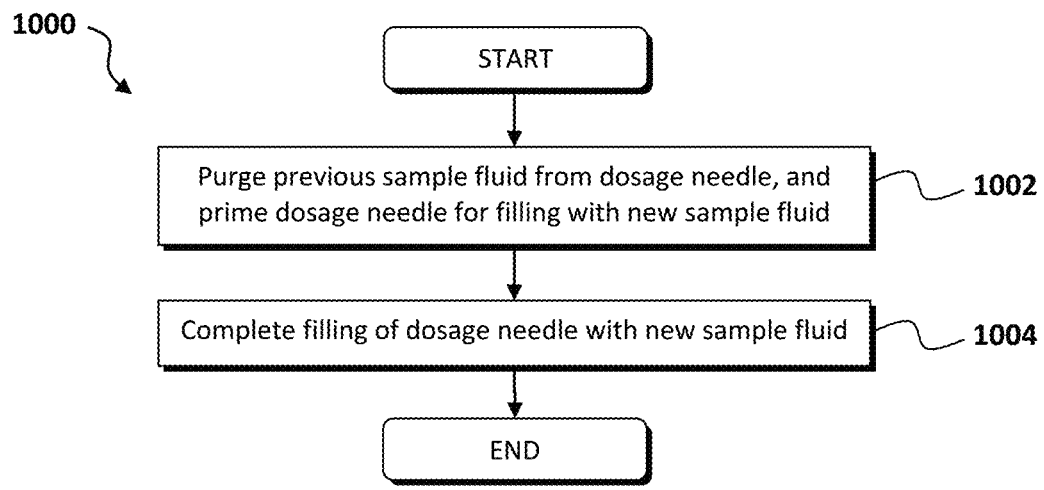
FIG. 10 is a flow diagram of a method 1000 of pre-preparation of a dosage needle.

FIG. 10 illustrates a method 1000 of pre-preparation of a dosage needle, more particularly prior to method 900, or in place of step 902 of method 900. In a first step 1002, sensor pump 218 is operated at a first pump rate to purge the previous sample fluid through the dosage needle 214 into the sample chamber 222, and draw the new sample fluid into the dosage needle 214. It is envisaged that this first pump rate may be relatively fast, to produce the filling condition illustrated in FIG. 4C as the result of wicking of the sample fluid once the sample pump 218 is stopped, thereby priming the dosage needle 214 for completion of filling to the tip as illustrated in FIG. 4A.

The sensor pump 218 may be stopped at a known position, for example a predetermined point in the rotation of a peristaltic pump. More particularly, in the case of a peristaltic pump the stopping position may be prior to a roller of the pump lifting off the tube of the pump, and such that the volume of sample fluid primed to be delivered to the dosage needle 214 sufficient to complete filling of the needle 214 and subsequently deliver a sample before the roller lifts. Lifting of the roller from the tube may produce a momentary disruption in the delivery of the sample fluid. It is envisaged that the accuracy and repeatability of the sample delivery may be improved by avoiding this position at times where greater precision is required, particularly in circumstances in which the sample volume is in the order of microlitres.

In a second step 1004, filling of the dosage needle 214 with new sample fluid for delivery to the sensing element (for example, bioresponsive element 204 of biosensor 202) may be completed (i.e. performing step 902 of method 900). It is envisaged that this may be achieved by operating the sensor pump 218 at a second pump rate, slower than the first pump rate, for a predetermined time to achieve the filling condition as illustrated in FIG. 4A, with any excess fluid being wicked away.

In an exemplary embodiment, the sample waste pump 228 may be operated to clear the purged sample during step 1002, but may be stopped prior to the sensor pump 218 being stopped (i.e. sensor pump 218 operates for a period after the sample waste pump 228 is stopped). More particularly, the waste pump 228 may be stopped prior to operating the sensor pump 218 at the second pump rate. It is envisaged that this may avoid producing a vacuum within the chamber as the dosage needle 214 is raised away from the docked position, which could otherwise draw sample fluid from the dosage needle to produce the filling condition as illustrated in FIG. 4C, rather than the level filling condition as illustrated in FIG. 4A.

Figure 11:
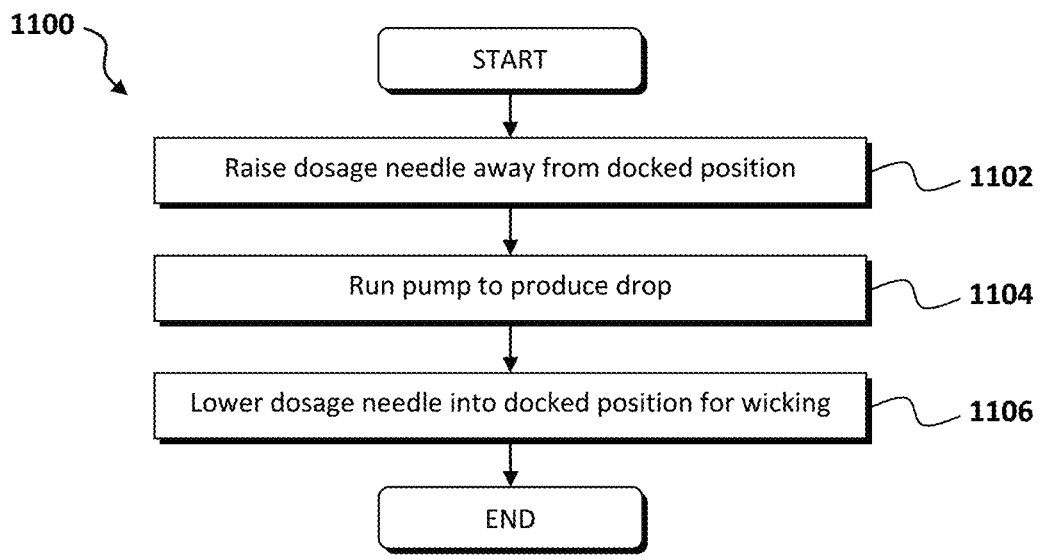
FIG. 11 is a flow diagram of a method 1100 of producing a drop at the tip of a dosage needle.

FIG. 11 illustrates a method 1100 of producing a drop at the tip of a dosage needle, more particularly for use with method 900 (for example, to perform step 902). In step 1102, the dosage needle 214 is raised away from a docked position in which the tip of the needle is proximate to the upright wall. In step 1104, a sample delivery pump (for example, sensor pump 218) is run for a predetermined period of time to produce a drop. In exemplary embodiments, prior to step 1102 the sensor pump 218 may be run to stop at a known position (for example, a particular point in the rotation of a peristaltic pump) in order to assist with improving the precision of the drop formed in step 1104. In step 1106 the dosage needle 214 is lowered into the docked position for wicking of the drop to produce the filling condition as illustrated in FIG. 4A.

Figure 12:
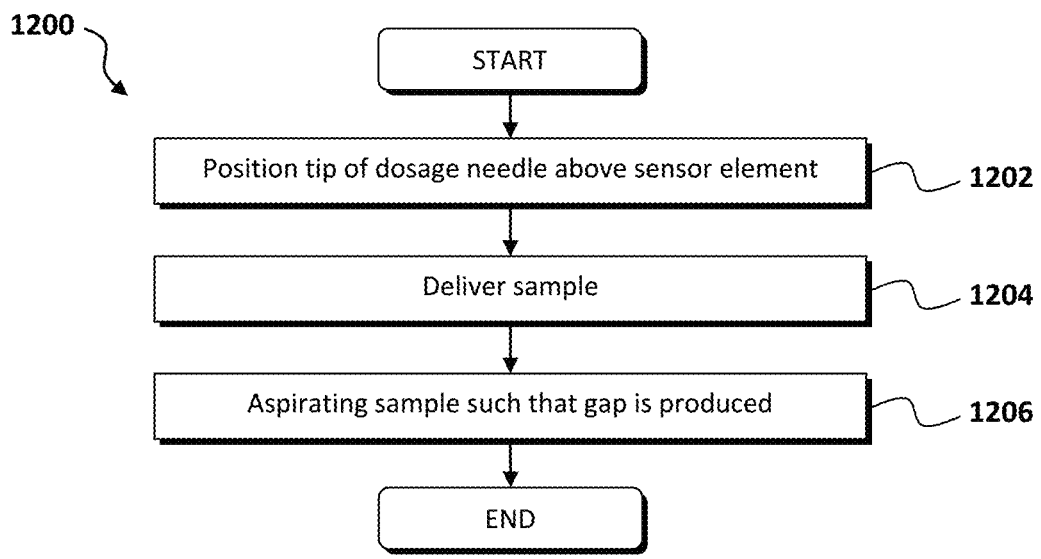
FIG. 12 is a flow diagram of a method 1200 of delivering a sample of fluid to a sensing element using a dosage needle.

FIG. 12 illustrates a method 1200 of delivering a sample of fluid to a sensing element (for example, bioresponsive element 204 of biosensor 202) using a dosage needle (for example, dosage needle 214). In exemplary embodiments, the method 1200 may be performed following performance of one or more of methods 900, 1000, and 1100. Method 1200 will be described herein with reference to FIG. 13A to 13C, which illustrate the tip of dosage needle 214 relative to a bioresponsive element in the form of an absorbent reactive pad 1300.

In a first step 1202, the tip of the dosage needle 214 is positioned at a predetermined height above the absorbent reactive pad 1300, with an air gap 1302 therebetween (for example, as shown in FIG. 13A). In step 1204, a fixed volume of sample fluid is delivered from the dosage needle 214—for example, by operating the sensor pump 218 for a predetermined period of time—such that the sample 1304 mounds up between the tip of the dosage needle 214 and the absorbent reactive pad 1300, held within the edges of the pad by natural surface tension (for example, as shown in FIG. 13B).

In step 1206, a portion of the sample fluid may be removed by aspirating the sample through the dosage needle 214 (for example, by reversing the sensor pump 218), until an air gap 1306 results with a residual layer 1308 of the sample fluid left on the absorbent reactive pad 1300. In exemplary embodiments, the method may include a step of providing a wait time between step 1204 and step 1206 to allow for partial absorption of the sample. The reaction of the absorbent reactive pad 1300 with the target analyte(s) of the sample fluid may then be analysed as known in the art of biosensors.

FIG. 14A, FIG. 14B and FIG. 14C illustrate alternative examples of dosage needles 214 which may be used with the method 1200, without a complete air gap between the dosage needle 214 and the absorbent reactive pad 1300. In these embodiments, each needle 214 includes at least one spacing feature which extends beyond a first point at which the bore of the needle 214 is opened to air—i.e. the spacing features prevent occlusion of the sample of fluid from the bore by the needle 214 pressing against the sensing element. It is envisaged that such spacing features may assist with achieving a consistent spatial relationship between the needle 214 and sensing element (for example, the absorbent reactive pad 1300), which in turn has an effect on providing a consistent residual volume of the sample fluid following aspiration.

It is envisaged that the spacing feature may be configured to not interfere with attaining a filling condition such as shown in FIG. 4A. For example, the spacing feature may be spaced radially from an internal rim of the needle bore.

FIG. 14A shows a first embodiment in which one or more spacer legs 1400 extend beyond the tip of the dosage needle 214. In the example illustrated the spacer leg 1400 is spaced laterally from the surface of the dosage needle 214 at which the bore exits (i.e. the surface containing the internal rim of the bore), although alternative examples are contemplated in which the spacer leg 1400 extends from that surface. It is also contemplated that the spacer leg 1400 may be provided away from the wicking feature, in use, to reduce the likelihood of interference with the wicking process in embodiments using this feature. FIG. 14B shows a second embodiment in which spacer recesses 1402 are provided in one or more sides of the dosage needle 214, with the remaining material of the needle 214 acting as a spacer. FIG. 14C shows a similar embodiment to FIG. 14B, in which the end of the needle 214 includes an inclined section 1404 such that one portion of the needle tip contacts the absorbent reactive pad 1300 while leaving an elevated point at which the bore (not illustrated) opens above the absorbent reactive pad 1300.

While not illustrated, it is also contemplated that the spacing feature may be provided on the sensing element side of the arrangement—i.e. the spacing feature acts as a stop against the dosage needle or an associated component to define the gap between the sensing element and the dosage needle.

FIG. 15 illustrates a method 1500 of cleaning a dosage needle (for example, dosage needle 214) and sample chamber (for example, sample chamber 222) in place. In first step 1502, the sample chamber 222 is filled with a cleaning fluid—for example, by extracting cleaning fluid from milk tube 204 during a cleaning cycle of the associated milking plant. Cleaning fluid reaching the overflow port 324 floods the associated tubing. It is envisaged that in environments in which the cleaning fluid is lower than an effective cleaning temperature for a particular application on reaching the chamber 222, a heating element may be provided for heating the cleaning fluid at the chamber, or prior to delivery to the chamber.

In a second step 1504, a negative pressure differential is produced within the chamber 222 to allow an inrush of air through duckbill valve 232 to produce turbulence in the cleaning fluid. For example, the sample waste pump 228 may be operated at a faster rate to the sensor pump 218.

In exemplary embodiments, steps 1502 and 1504 may be performed a plurality of times. It is envisaged that this may be performed by continuously operating the sensor pump 218, and cycling operation of the sample waste pump 228.

For completeness, it is reiterated that while aspects of the present technology are described in the context of biosensors used for sensing of milk, alternative embodiments are expressly contemplated. By way of example, the present technology may be used in the sampling and sensing of environmental pollutants in waterways or ground water, water quality indicators in municipal water supply or waste water outlets, or spoilage indicators in food and beverage processing plants.

For a firmware and/or software (also known as a computer program) implementation, the techniques of the present disclosure may be implemented as instructions (for example, procedures, functions, and so on) that perform the functions described. It should be appreciated that the present disclosure is not described with reference to any particular programming languages, and that a variety of programming languages could be used to implement the present invention. The firmware and/or software codes may be stored in a memory, or embodied in any other processor readable medium, and executed by a processor or processors. The memory may be implemented within the processor or external to the processor.

A processor may be a microprocessor, but in the alternative, the processor may be any processor, controller, microcontroller, state machine, or cloud computing device known in the art. A processor may also be implemented as a combination of computing devices, for example, a combination of a digital signal processor (DSP) and a microprocessor, a plurality of microprocessors, one or more microprocessors in conjunction with a DSP core, or any other such configuration.

The processors may function in conjunction with servers and network connections as known in the art. By way of example, the biosensor system and a central processor may communicate with each other over a Controller Area Network (CAN) bus system. In the context of milking, performance sensors, animal identification devices, and milking plant sensors may also communicate with the central processor. In an exemplary embodiment, animal identifiers, data from the sensors, and any other data may be stored in a data cloud.

The steps of a method, process, or algorithm described in connection with the present disclosure may be embodied directly in hardware, in a software module executed by one or more processors, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

Unless the context clearly requires otherwise, throughout the description and the claims, the words "comprise", "include", "comprising", "including", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference. Reference to any prior art in this specification is not, and should not be taken as, an acknowledgement or any form of suggestion that that prior art forms part of the common general knowledge in the field of endeavour in any country in the world. The discussion of the references states what their authors assert, and the applicant reserves the right to challenge the accuracy and pertinency of the cited documents.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently disclosed embodiments described herein will be apparent to those skilled in the art. Such changes and modifications may be made without departing from the spirit and scope of the disclosure and without diminishing its attendant advantages. It is therefore intended that such changes and modifications be included within the present disclosure.

The invention claimed is:

1. A system for analysing a fluid, including:
   a sensing element configured to respond to at least one analyte in a sample of fluid;
   a detector configured to sense a response to the analyte by the sensing element;
   a fluid sample delivery apparatus, including:
      a dosage needle configured to deliver the sample of fluid to the sensing element;
      at least one pump configured to control flow of fluid through the dosage needle;
      at least one actuator configured to move the dosage needle relative to the sensing element; and
      a wicking feature configured to contact a drop of the same fluid as the sample of fluid suspended from the dosage needle when the dosage needle is in a predetermined position relative to the wicking feature; and
   at least one controller configured to:
   control the at least one actuator to position the dosage needle relative to the sensing element such that a gap is provided between at least a portion of an end of the dosage needle from which the sample of fluid is delivered and the sensing element;
   control the at least one pump to deliver a predetermined volume of the sample of fluid to the sensing element through the dosage needle;
   control the at least one pump to control aspiration of at least a portion of the sample of fluid back from the sensing element; and
   prepare the sample of fluid in the dosage needle prior to delivery to the sensing element, including positioning the dosage needle proximate to the wicking feature, such that the drop of the same fluid as the sample of fluid is wicked away from the dosage needle by the wicking feature.

2. The system of claim 1, wherein the at least one controller is configured to control aspiration of the sample fluid from the sensing element such that an air gap is produced between at least a portion of an end of the dosage needle and residual sample fluid on the sensing element.

3. The system of claim 1, wherein the at least one controller is configured to initiate aspiration of the sample of fluid after a predetermined period of time following delivery of the predetermined volume of the sample of fluid.

4. The system of claim 1, wherein the system is configured such that the end of the dosage needle at which the drop is formed is laterally spaced from the wicking feature when positioned to be proximate to the wicking feature.

5. The system of claim 1, including a chamber having an upper wall having an aperture configured to receive the dosage needle.

6. The system of claim 5, wherein the at least one controller is configured to form a drop on the end of the dosage needle prior to insertion into the aperture of the chamber.

7. The system of claim 5, including a wicking feature configured to contact a drop of the same fluid as the sample of fluid suspended from the dosage needle when the dosage needle is in a predetermined position relative to the wicking feature, wherein an inner surface of the upper wall is sloped downwardly towards the wicking feature.

8. The system of claim 5, wherein the chamber includes:
   a waste port positioned at a lowermost point in the chamber;
   a waste pump provided to the waste port;
   an overflow port positioned above the aperture in the upper wall; and
   an overflow valve provided to the overflow port to prevent backflow into the chamber through the overflow port.

9. The system of claim 8, wherein the chamber includes an air bleed valve configured to permit inflow of air to provide pressure equalisation.

10. The system of claim 1, wherein the dosage needle includes a barrel portion having a tip from which the sample of fluid is delivered, and a seal provided on an exterior of the barrel portion.

11. The system of claim 1, wherein the sensing element is a bioresponsive element.

12. The system of claim 1, wherein the sensing element is configured to provide an optically detectable reaction in response to the at least one analyte.

13. The system of claim 1, wherein the sensing element includes an absorbent pad.

14. The system of claim 1, wherein the at least one pump is a peristaltic pump.

15. A method for analysing a fluid, including:
   moving, using at least one actuator, a dosage needle of a fluid sample delivery device relative to a sensing element;
   delivering a sample of fluid to the sensing element via the dosage needle by controlling at least one pump configured to control flow of fluid through the dosage needle, wherein the sensing element is configured to respond to at least one analyte in the sample of fluid; and
   sensing, using a detector, a response to the at least one analyte by the sensing element, wherein delivering the sample of fluid includes:
   preparing the sample of fluid in the dosage needle prior to delivery to the sensing element, wherein preparing the sample of fluid includes positioning the dosage needle proximate to a wicking feature, such that a drop of the same fluid as the sample of fluid formed on a tip of the dosage needle is wicked away from the dosage needle by the wicking feature;
   positioning the dosage needle relative to the sensing element such that a gap is provided between at least a portion of an end of the dosage needle from which the sample of fluid is delivered and the sensing element;
   delivering the sample of fluid as a predetermined volume of the sample of fluid to the sensing element through the dosage needle;
   aspirating at least a portion of the sample of fluid back from the sensing element.

* * * * *